United States Patent
Talos et al.

[11] Patent Number: 5,709,686
[45] Date of Patent: Jan. 20, 1998

[54] BONE PLATE

[75] Inventors: Gilbert Talos, Oberdorf; Roland Schmoker, Bern, both of Switzerland

[73] Assignee: Synthes (U.S.A.), Paoli, Pa.

[21] Appl. No.: 750,114

[22] PCT Filed: Mar. 27, 1995

[86] PCT No.: PCT/CH95/00065
§ 371 Date: Nov. 26, 1996
§ 102(e) Date: Nov. 26, 1996

[87] PCT Pub. No.: WO96/29948
PCT Pub. Date: Oct. 3, 1996

[51] Int. Cl.⁶ .................................................. A61B 17/80
[52] U.S. Cl. ..................................... 606/69; 606/73
[58] Field of Search .................... 606/69, 70, 71, 606/72, 73

[56] References Cited

U.S. PATENT DOCUMENTS

| | | |
|---|---|---|
| 4,493,317 | 1/1985 | Klaue ............................ 128/92 |
| 5,002,544 | 3/1991 | Klaue et al. ..................... 606/69 |
| 5,041,113 | 8/1991 | Biedermann et al. ............ 606/61 |
| 5,085,660 | 2/1992 | Lin ................................. 606/73 |

FOREIGN PATENT DOCUMENTS

| | | |
|---|---|---|
| 0 053 999 A1 | 6/1982 | European Pat. Off. . |
| 0 410 309 A1 | 1/1991 | European Pat. Off. . |
| 2 674 118 | 9/1992 | France . |
| WO 88/03781 | 6/1988 | WIPO . |

*Primary Examiner*—Gary Jackson
*Assistant Examiner*—David O. Reip
*Attorney, Agent, or Firm*—Pennie & Edmonds LLP

[57] ABSTRACT

The invention concerns a bone plate comprising holes (2) running in the longitudinal plate direction and receiving bone screws. The major axis $D_L$ as seen in the direction of the longitudinal plate axis (1) of at least one hole (2) is larger than the minor axis $D_Q$ of this hole (2) running perpendicularly to the plate longitudinal axis (1). At least one of these holes (2) evincing a minor axis $D_Q$ perpendicular to the plate axis (1) comprises a partial thread (3) in the area of this minor axis $D_Q$ to receive a bone screw with a thread head.

14 Claims, 4 Drawing Sheets

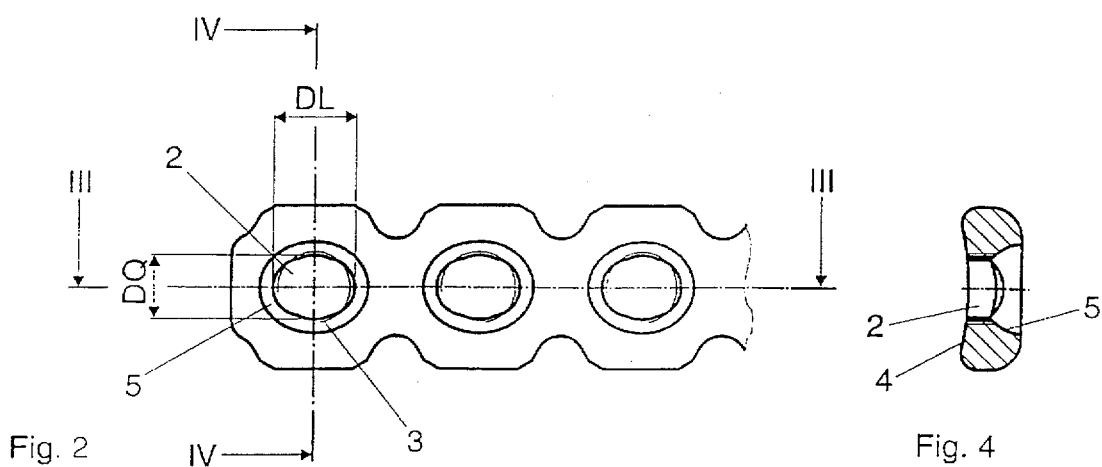
Fig. 2
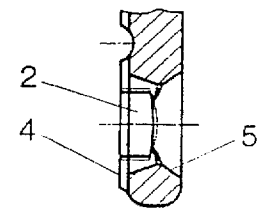
Fig. 4
Fig. 3

BONE PLATE

TECHNICAL FIELD

The invention concerns a bone plate for stabilizing and/or compressing a bone.

BACKGROUND OF THE INVENTION

A bone plate is known from French patent document 742,618 wherein circular boreholes in the plate slant relative to a normal to the plate and are fitted with inside threads. These boreholes accept bone screws fitted with a second threaded portion which is widened compared to the conventional threaded screw shank segment and corresponding to the inside thread of the plate boreholes. Because of the slant of the plate boreholes, the bone screws also can be anchored at a slant, determined by said boreholes, into the bone.

The known bone plate incurs the drawback that the slant of the bone screws cannot be selected at will but instead is predetermined by the slant of the boreholes and their inside thread.

SUMMARY OF THE INVENTION

The object of the invention is palliation and to create a bone plate of which the boreholes are designed selectively to make possible two different kinds of screw anchorings. In the first application, a bone screw with a spherical head may be screwed into an elongated slot of the plate within a wide and selectable range at an angle to the plate normal into the bone. By tilting the countersink of the plate boreholes, furthermore a compressive effect is made possible.

In the second application a bone screw with a head thread and in the form of a bracing screw can be vertically and rigidly screwed into the plate at the partial inside thread of the elongated slot.

The invention achieves its object by a bone including an elongated plate defining a longitudinal axis along its length. The bone plate has an upper surface and a lower surface for application to a bone. A plurality of elongated holes are arranged along the length of the plate for receiving bone screws. At least one of the elongated holes has a first diameter $D_L$, which is measured along the length of the hole. A second diameter $D_Q$ is measured across the width of the hole. Advantageously, $D_L$ is greater than $D_Q$ and at least one of the elongated holes includes a partial threaded portion arranged in the area of diameter $D_Q$. The threaded portion is configured for seating a bone screw which has a threaded head.

Essentially, the advantages offered by the invention are that the bone plate of this invention are ubiquitously applicable in the most diverse cases such as fixation, compression, and employment as fixateur interne (internal affixer) in the sense of a bracing screw, but especially in the maxillofacial field requiring three-dimensional matching.

The invention offers also the following advantages
compatibility with conventional cortical screws,
variable angular orientation of the bone screws in the plate boreholes
problem-free removal of bone screws even in the case of intra-oral access,
possibility of new operation using a new plate,
screw head affixation in the plate borehole using bone screws of conventional diameter, and
achieving compression using screws with spherical heads.

BRIEF DESCRIPTION OF THE DRAWINGS

The invention and further embodiments of this invention are elucidated below in relation to partly diagrammatic drawings of an illustrative embodiment wherein.

FIG. 2 is a partial top view of the bone plate of the invention, FIG. 3 is a partial longitudinal section of the bone plate along line III—III of FIG. 2, FIG. 4 is a cross-section orthogonal to the bone-plate longitudinal direction along line IV—IV of FIG. 2.

DETAILED DESCRIPTION OF THE PREFERRED EMBODIMENTS

Figure 1:
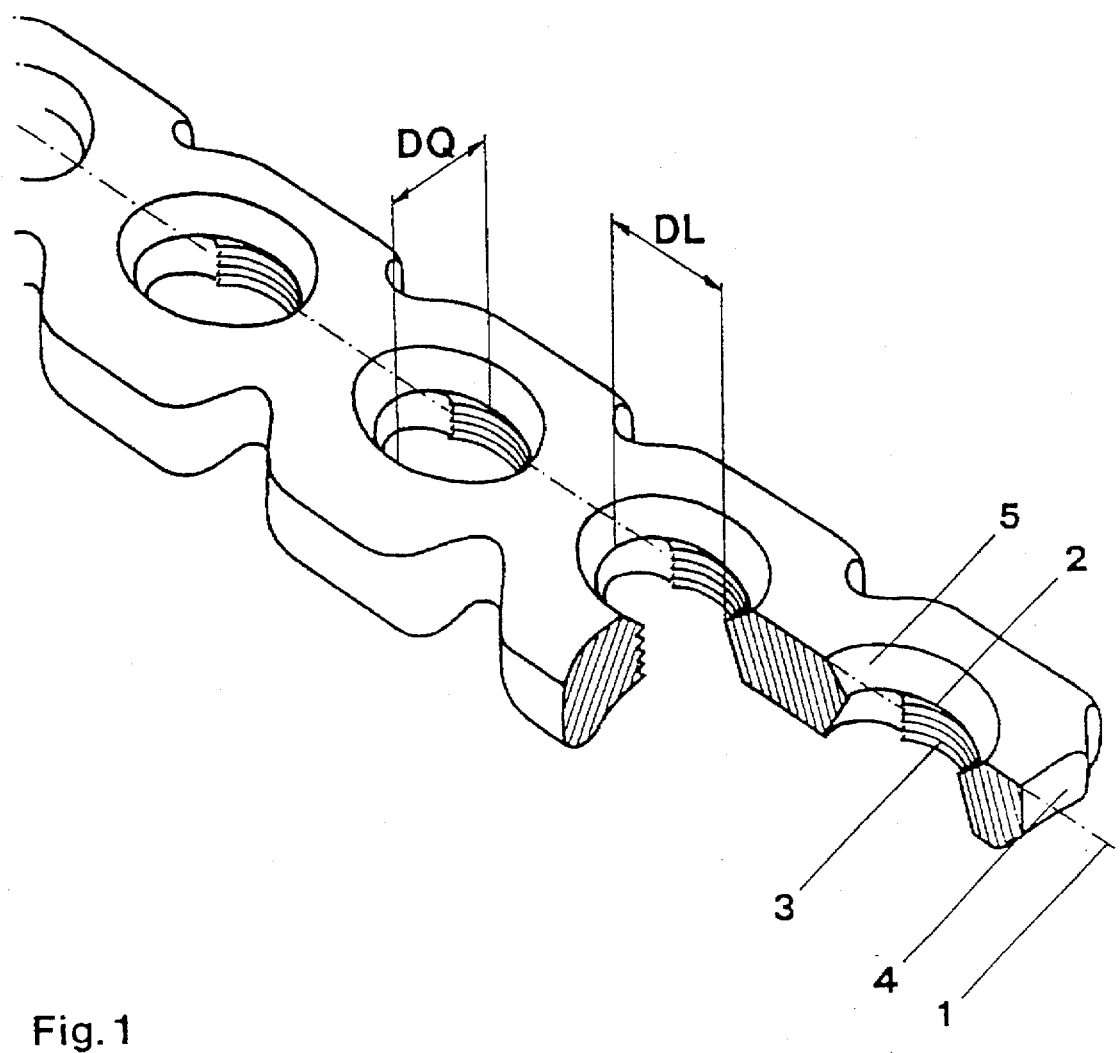
FIG. 1 is a partial perspective of a bone plate of the invention.

The bone plate shown in FIG. 1 comprises several holes 2 to receive diverse types of bone screws 6, 7 (shown in FIGS. 5, 6) with which to affix the bone plate to the bone.

As shown in detail in FIGS. 2–4, the holes 2 are designed to be so-called elongated slots, that is, when measured in the direction of the plate longitudinal axis 1 the major axis $D_L$ is larger than the minor axis $D_Q$ perpendicular to the plate longitudinal axis 1. $D_L/D_Q$ is preferably within the range of 1.01 to 3 and most preferably within the range of 1.1 to 1.5.

As shown in FIG. 4, the lower part of the hole 2 facing the bone application surface 4 is approximately circular in the direction transverse to the plate and, as shown in FIG. 3, it flares approximately conically in the plate longitudinal direction toward the bone application surface 4. An inside thread is in the circular segment of the hole 2 and, because of design constraints, runs only in the lateral part of the plate over an angular range of about 60° to 179°, preferably about 90° to 150°.

Figure 5:
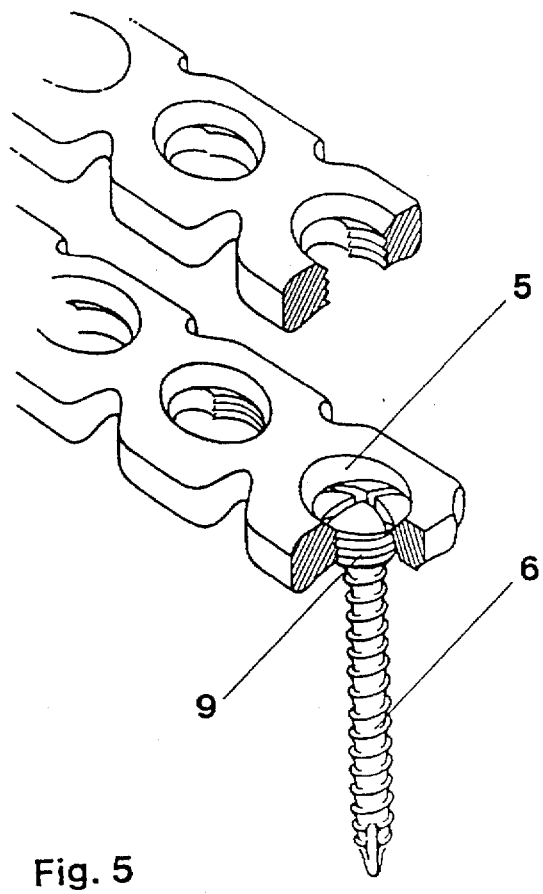
FIG. 5 is a partial longitudinal section of a bone plate of the invention with a double-threaded bone screw which is screwed-in perpendicularly.

As shown in FIG. 5, this partial inside thread is used to receive a bone screw 6 with a thread-head 9. By screwing the outside thread of the thread-head 9 into the corresponding and partial inside thread 3, rigid anchoring of bone screw 6 into the plate is achieved. Such screwed-in bone screw 6 serves as a bracing screw.

Figure 6:
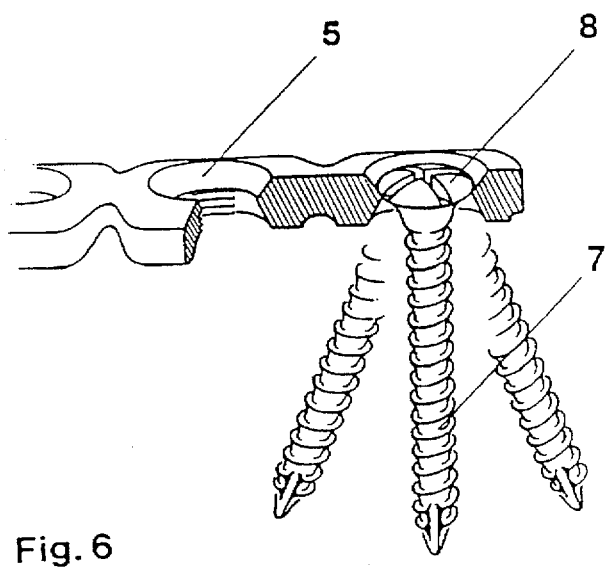
FIG. 6 is a partial longitudinal section of a bone plate of the invention with a bone screw passing through the plate perpendicularly or at a slant, said bone screw comprising a spherical head and serving as a non-compressive affixation screw.
Figure 7:
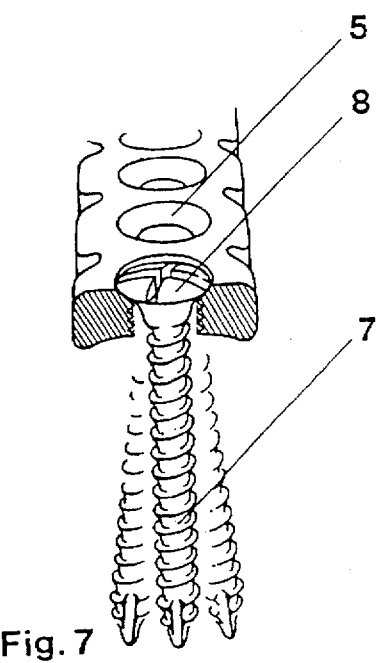
FIG. 7 is a cross-section perpendicular to the longitudinal section of FIG. 6 and located in the hole area of the bone plate.

The upper part of hole 2 away from bone contact surface 4 is oval and comprises a conical flaring countersink area which, as shown in FIGS. 6, 7, slidingly receives a bone screw 7 with a spherical head 8. The expression "bone application surface" 4 denotes the plate surface which substantially directly contacts the bone.

Figure 8:
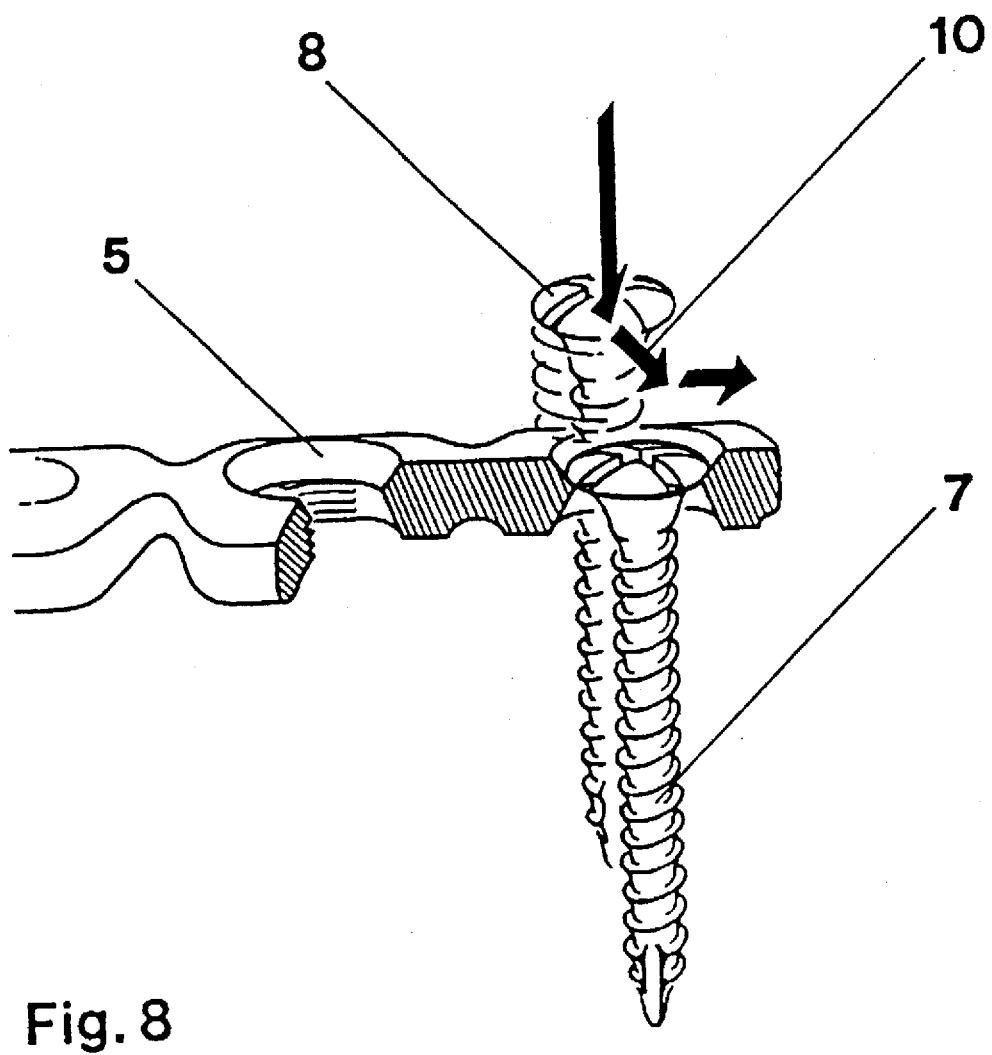
FIG. 8 is a partial longitudinal section of a bone plate of the invention through which passes a perpendicular bone screw with a spherical head and serving as a compressive affixation screw.

Similarly to FIGS. 6 and 7, FIG. 8 shows a bone plate fitted with a bone screw 7 comprising a spherical head 8, the plate, as indicated by the arrow 10, being able to generate compression. For that purpose the conically flaring area 5 of the hole 2 (as shown in FIG. 3), is machined by a spherical or bevelling miller at an angle of 57° relative to the plate longitudinal axis 1, whereby the elongated slot so produced acts like a ramp for the bone screw 7.

The special geometry of the hole 2 allows selective use of various types of bone screws 6, 7 on one and the same bone plate.

What is claimed is:

1. A bone plate comprising:

an elongated plate defining a longitudinal axis along its length having an upper surface, a lower surface for application to a bone, and a plurality of elongated holes arranged along the length of the plate for receiving bone screws, said elongated holes being oblong in shape and having a major axis $D_L$ and a minor axis $D_Q$, with $D_L$ being greater than $D_Q$, wherein at least one of said elongated holes includes partial threaded portions arranged on an inner wall of the elongated hole, and is configured for seating a bone screw having a threaded head.

2. The bone plate of claim 1, wherein each elongated hole has a lower part which extends to the lower surface of the plate, and an upper part which extends to the upper surface of the plate, and the partial threaded portion is positioned in the lower part of the elongated hole.

3. The bone plate of claim 2, wherein the lower part of said at least one elongated hole includes a flared surface which extends outwardly to the lower surface of the bone plate.

4. The bone plate of claim 3, wherein the partial threaded portions extend around opposing portions of the inner wall in an area of the minor axis, and the lower flared surface extends outwardly adjacent to the partial threaded portions.

5. The bone plate of claim 3, wherein said lower flared surface is conically shaped.

6. The bone plate of claim 2, wherein said at least one elongated hole further comprises an outwardly flared countersink surface adjacent the upper surface for slidingly receiving a bone screw having a spherical head.

7. The bone plate of claim 6, wherein the outwardly flared countersink surface is shaped and configured for mating engagement with the bone screw.

8. The bone plate of claim 6, wherein the outwardly flared countersink surface has an angle relative to the longitudinal axis of the plate which is sufficient to produce a ramping effect for engagement with a bone screw.

9. The bone plate of claim 8, wherein the outwardly flared countersink surface has an angle of 57°.

10. A method for compressing a bone using the bone plate of claim 6, comprising:

positioning said bone plate on a surface;

inserting a bone screw having a spherical head into at least one elongated hole at one end of said hole; and screwing said bone screw into the surface so that as the spherical head of the screw contacts the outwardly flared countersink surface of the hole, the spherical head of the screw ramps downwardly along the flared surface to move the plate to generate compression.

11. The bone plate of claim 1, wherein $D_L/D_Q$ is within the range of 1.01 to 3.

12. The bone plate of claim 1, wherein $D_L/D_Q$ is within the range of 1.1 to 1.5.

13. The bone plate of claim 1, wherein the major axis of at least one of said elongated holes is positioned along the longitudinal axis of the plate.

14. The bone plate of claim 1, wherein the lower surface has a curved shape for contacting a bone.

* * * * *